(12) United States Patent
Urban

(10) Patent No.: US 11,076,621 B2
(45) Date of Patent: Aug. 3, 2021

(54) REMEDIATION OF TOXINS IN BIOREFINERY PROCESS STREAMS

(71) Applicant: POET Research, Inc., Sioux Falls, SD (US)

(72) Inventor: Shannon Scott Urban, Valley Springs, SD (US)

(73) Assignee: POET Research, Inc., Sioux Falls, SD (US)

( * ) Notice: Subject to any disclaimer, the term of this patent is extended or adjusted under 35 U.S.C. 154(b) by 158 days.

(21) Appl. No.: 16/050,681

(22) Filed: Jul. 31, 2018

(65) Prior Publication Data

US 2019/0029296 A1  Jan. 31, 2019

Related U.S. Application Data

(60) Provisional application No. 62/539,226, filed on Jul. 31, 2017.

(51) Int. Cl.
| | | |
|---|---|---|
| *A23L 5/20* | (2016.01) | |
| *C12H 1/00* | (2006.01) | |
| *B01J 19/00* | (2006.01) | |
| *C12P 7/06* | (2006.01) | |
| *C12F 3/06* | (2006.01) | |

(52) U.S. Cl.
CPC .......... *A23L 5/276* (2016.08); *B01J 19/0033* (2013.01); *C12H 1/00* (2013.01); *C12P 7/06* (2013.01); *C12F 3/06* (2013.01)

(58) Field of Classification Search
CPC ...... C12P 7/06; A23L 5/20; A23L 7/00; A23L 5/276; B01J 19/0033; C12H 1/00; C12H 1/14

See application file for complete search history.

(56) References Cited

U.S. PATENT DOCUMENTS

| | | |
|---|---|---|
| 4,092,434 A | 5/1978 | Yoshizumi et al. |
| 4,316,956 A | 2/1982 | Liitzen |
| 7,842,484 B2 | 11/2010 | Lewis |
| 7,919,291 B2 | 4/2011 | Lewis et al. |
| 8,409,640 B2 | 4/2013 | Lewis et al. |
| 8,470,550 B2 | 6/2013 | Lewis |
| 8,597,919 B2 | 12/2013 | Lewis |
| 8,679,793 B2 | 3/2014 | Lewis |
| 8,702,819 B2 | 4/2014 | Bootsma |
| 8,748,141 B2 | 6/2014 | Lewis et al. |
| 9,901,108 B2 | 2/2018 | Mann et al. |
| 9,902,830 B2 | 2/2018 | Yiannikouris et al. |
| 10,131,866 B2 | 11/2018 | Elend et al. |
| 10,149,489 B2 | 12/2018 | Fruhauf et al. |
| 10,450,271 B2 | 10/2019 | Trail et al. |
| 10,531,662 B2 | 1/2020 | Strasburg et al. |
| 10,598,661 B2 | 3/2020 | Sarver, Jr. et al. |
| 10,721,950 B2 | 7/2020 | Cecava et al. |
| 2015/0376558 A1* | 12/2015 | Elend .................. A23K 10/38 426/12 |
| 2018/0092950 A1 | 4/2018 | Davis et al. |
| 2018/0279616 A1 | 10/2018 | Dahmen et al. |
| 2018/0298352 A1 | 10/2018 | Torres Acosta et al. |
| 2018/0325936 A1 | 11/2018 | Marquardt et al. |
| 2019/0293527 A1 | 9/2019 | Jabour et al. |
| 2020/0029575 A1 | 1/2020 | Trail et al. |
| 2020/0236965 A1 | 7/2020 | Bianchini et al. |

FOREIGN PATENT DOCUMENTS

| | | |
|---|---|---|
| EP | 2 677 881 B1 | 1/2014 |
| EP | 3 157 538 B1 | 4/2017 |
| WO | 2011100165 A1 | 8/2011 |
| WO | 2013086548 A2 | 6/2013 |
| WO | 2017044624 A1 | 3/2017 |
| WO | 2018113743 A1 | 6/2018 |
| WO | 2019034567 A1 | 2/2019 |
| WO | 2019046954 A1 | 3/2019 |
| WO | 2019162362 A1 | 8/2019 |
| WO | 2020025580 A1 | 2/2020 |

OTHER PUBLICATIONS

Karlovsky et al., Impact of Food Processing and Detoxification Treatments on Mycotoxin Contamination, Mycotoxin Re 32:179-205. (Year: 2016).*

International Search Report dated Sep. 25, 2018, for International application No. PCT/US2018/044556, 5 pages.

PCT Written Opinion dated Sep. 25, 2018 for International application No. PCT/US2018/044556, 10 pages.

Moerck et al., (1980) "Aflatoxin Destruction in Corn Using Sodium Bisulfite, Sodium Hydroxide and Aqueous Ammonia", Journal of Food Protection, 43(7): 571-574.

Young, J.C., (1986) "Reduction in Levels of Deoxynivalenol in Contaminated Corn by Chemical and Physical Treatment", J. Agric. Food Chem., 34(3): 465-467.

Young et al., (1986) "Reduction in Levels of Deoxynivalenol in Contaminated Wheat by Chemical and Physical Treatment", J. Agric. Food Chem., 34(3): 461-465.

Young et al., (1987 "Detoxification of Deoxynivalenol with Sodium Bisulfite and Evaluation of the Effects When Pure Mycotoxin or Contaminated Corn Was Treated and Given to Pigs", J. Agric. Food Chem., 35(2): 259-261.

\* cited by examiner

*Primary Examiner* — Hong T Yoo

(74) *Attorney, Agent, or Firm* — Kagan Binder, PLLC

(57) ABSTRACT

Provided are methods and systems for remediating toxins present in feedstock that are used in processes to produce ethanol and other products.

18 Claims, 6 Drawing Sheets

REMEDIATION OF TOXINS IN BIOREFINERY PROCESS STREAMS

CROSS REFERENCE TO RELATED APPLICATIONS

This application claims the benefit of U.S. Provisional Patent Application Ser. No. 62/539,226, filed Jul. 31, 2017, the disclosure of which is incorporated in its entirety herein by reference.

FIELD OF THE INVENTION

The invention relates to systems and methods for remediation of toxins in biorefinery process streams.

BACKGROUND

Cereal grains are often used as feedstock for the production of target chemicals in a biorefinery. The cereal grains are typically milled and further processed to convert starch and/or cellulose contained in the grains into fermentable sugars. The sugars are then converted into the target chemicals by microorganisms, such as yeasts, in a fermentation process. The fermentation product includes the target chemical and other materials which may include for example, water and other components such as oils, proteins, and residual carbohydrates including starches, sugars, and fiber. The target chemical is separated from the fermentation product and the other components are often collected as one or more co-products. An important class of co-products is nutritional products. The value of nutritional co-products is affected by contaminants that pass through the biorefinery process and into the co-product. For example, cereal grains can become infected with pathogens that produce a variety of toxins known as mycotoxins. There are many mycotoxins including, for example, various aflatoxins, ochratoxin, citrinin, ergo alkaloids, patulin, and fusarium toxins including for example zearalenone, deoxynivalenol, and fumonisin among others. The presence or severity of toxins in cereal grains is affected by the growing conditions for a particular location in a particular year. What is needed is an economical way to effectively reduce or eliminate toxins from biorefinery co-products.

The present invention provides for the remediation of toxins in biorefinery co-products by treating biorefinery process streams with a toxin mitigant.

The biorefinery feedstock may include cereal grains such as, for example, corn, wheat, sorghum, and rice among others.

The remediation may involve, for example, introducing a treatment compound into one or more process streams during or between process steps that will react with the toxin. For example, the treatment compound may be a sulfur containing compound such as a sulfate, sulfite, bisulfite, metabisulfite, and others. For example, the treatment compound may be ammonium bisulfite, potassium bisulfite, sodium bisulfite, and others. These compounds will react with some toxins to form less toxic or non-toxic sulfur compounds. For example, deoxynivalenol (DON) will react with sodium bisulfite to form sulfonated derivative of DON, termed as DON sulfonate or DONS.

Process steps may include one or more of inputting feedstock into the biorefinery, milling the feedstock to a meal or flour, mixing of the milled material with water to form a slurry, heating of the slurry to liquefy one or more components of the slurry, enzymatically hydrolyzing components of the slurry, fermenting the slurry, collecting the fermentation product, separating the fermentation product into different components, collecting fermentation product streams, dewatering, and collecting co-products. Not all of these steps need be used in any particular biorefinery operation.

SUMMARY

The present invention provides for the remediation of toxins in biorefinery co-products by treating biorefinery process streams with a toxin mitigant.

The biorefinery feedstock may include cereal grains such as, for example, corn, wheat, sorghum, and rice among others.

The remediation may involve, for example, introducing a treatment compound into one or more process streams during or between process steps that will react with the toxin. For example, the treatment compound may be a sulfur containing compound such as a sulfate, sulfite, bisulfite, metabisulfite, and others. For example, the treatment compound may be ammonium bisulfite, potassium bisulfite, sodium bisulfite, and others. These compounds will react with some toxins to form less toxic or non-toxic compounds. For example, deoxynivalenol (DON) will react with sodium bisulfite to form sulfonated derivative of DON, termed as DON sulfonate or DONS.

Process steps may include one or more of inputting feedstock into the biorefinery, milling the feedstock to a meal or flour, mixing of the milled material with water to form a slurry, heating of the slurry to liquefy one or more components of the slurry, enzymatically hydrolyzing components of the slurry, fermenting the slurry, collecting the fermentation product, separating the fermentation product into different components, collecting fermentation product streams, dewatering, and collecting co-products. Not all of these steps need be used in any particular biorefinery operation.

In one aspect of the invention is a process for remediating mycotoxin in one or more biorefinery process streams, wherein the process comprises introducing one or more treatment compounds into at least one grain biorefinery process stream to form a treated grain biorefinery process stream, wherein the at least one grain biorefinery process stream comprises a mycotoxin in a first amount, wherein the one or more treatment compounds react with the mycotoxin to form a treated mycotoxin, and wherein the treated grain biorefinery process stream comprises the mycotoxin in a second amount, wherein the second amount is less than the first amount.

In another aspect of the invention is a system for remediating toxins comprising: a reactant storage system comprising one or more treatment compounds; and a metering system in fluid communication with the reactant storage system, wherein the system is adapted to be coupled to one or more grain biorefinery process streams to add a controlled amount of the one or more treatment compounds into the one or more grain biorefinery process streams, to produce a treated grain biorefinery process stream, wherein the at least one grain biorefinery process stream comprises a mycotoxin in a first amount, wherein the one or more treatment compounds reacts with the mycotoxin to form a treated mycotoxin, and wherein the treated grain biorefinery process stream comprises the mycotoxin in a second amount, wherein the second amount is less than the first amount.

BRIEF DESCRIPTION OF THE DRAWINGS

Various examples of the present invention will be discussed with reference to the appended drawings. These drawings depict only illustrative examples of the invention and are not to be considered limiting of its scope.

DESCRIPTION

Described herein are methods and systems to reduce the toxicity, the concentration, or both (referred herein as "remediation") of one or more toxins present in feedstock used in biorefinery processes. "Biorefinery" as used herein refers to a facility that processes biological material (such as seed, grain, crop waste or feedstock) to produce products such as ethanol, and other products such as animal feed (dried distiller's grain).

Figure 1:
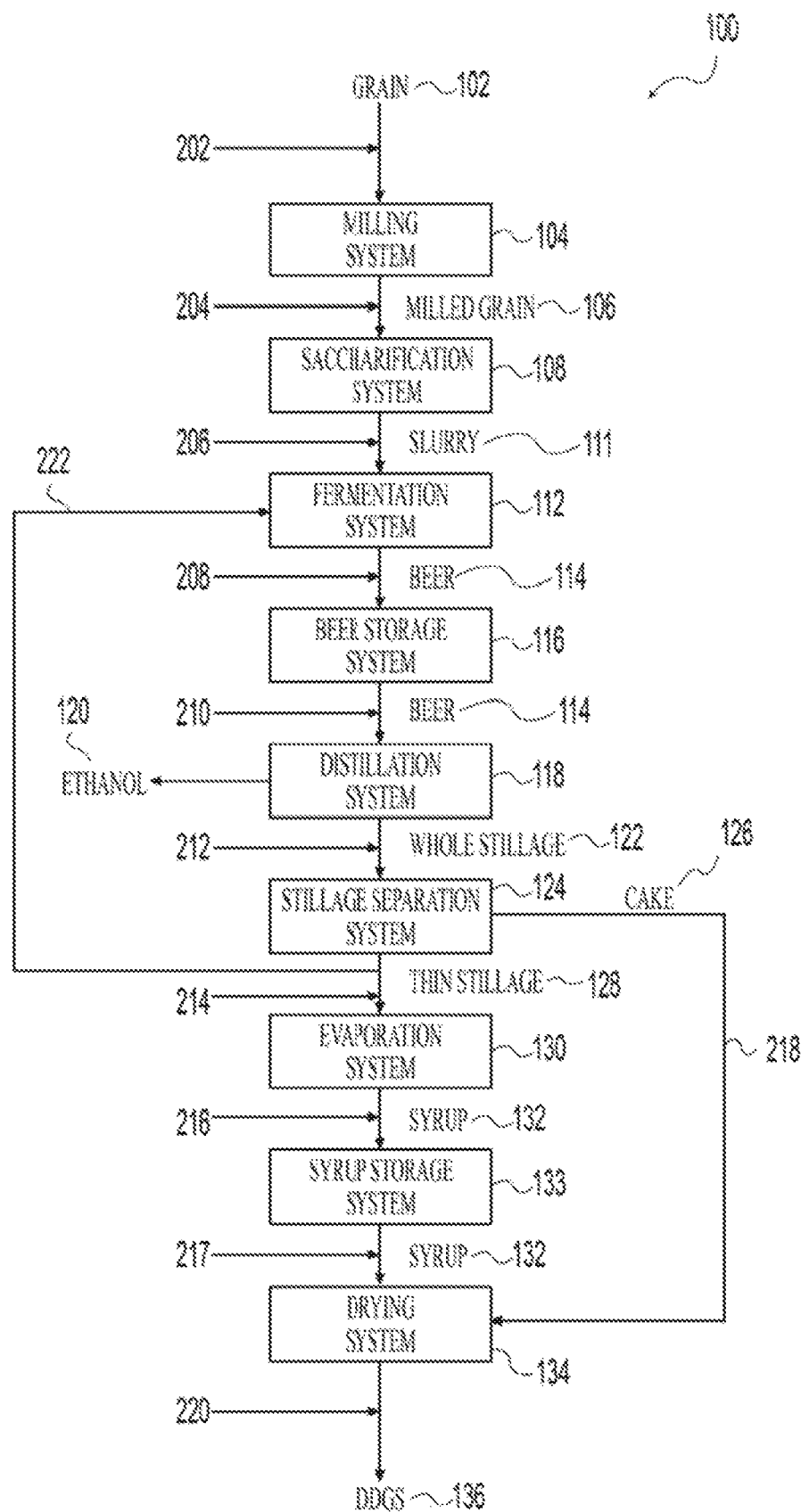
FIG. 1 is a flow diagram of a cereal grain-to-ethanol conversion process.

One example of the invention is shown in FIG. 1 depicting an ethanol biorefinery operation 100 that produces animal feed as a co-product. Grain 102 that has been contaminated with toxin is used as feedstock for the production of ethanol in the biorefinery. The grain 102 is reduced in size in a milling system 104. The milled grain 106 is mixed with water and further treated, for example thermally and/or enzymatically, to convert starch and fiber into fermentable sugars in a saccharification system 108. The resulting slurry 111 is combined with an ethanologen (e.g. yeast) to convert the sugars into ethanol in a fermentation system 112. In embodiments, the saccharification and fermentation can occur simultaneously in a single system (e.g. in an SSF fermentation system). The fermentation product, or beer 114, includes ethanol, water, oil, dissolved solids, toxin, protein, yeast, and residual carbohydrates including starch, sugar, and fiber. The beer 114 may be collected in a beer storage system 116 prior to further processing. The beer 114 is distilled in a distillation system 118 to separate the ethanol 120 from the other components, called whole stillage 122, of the beer 114. The whole stillage 122 is processed in a stillage separation system 124 into cake 126 and thin stillage 128. The cake 126 contains more of the solid particulate matter from the beer 114 including fiber, protein, yeast, and residual solid starch and some liquid including water, oil, and dissolved solids. The thin stillage 128 contains more of the liquid from the beer 114 including water, oil, and dissolved solids. The toxin is distributed in the cake 126 and thin stillage 128. However, because the toxin is water soluble, more of it is contained in the thin stillage 128. The thin stillage 128 is concentrated in an evaporation system 130 to form syrup 132. The syrup 132 may be collected in a syrup storage system 133 prior to further processing. The syrup 132 and cake 126 may be combined and dried in a drying system 134 to produce dried distillers grain with solubles (DDGS) 136. Examples of biorefinery operations are described in U.S. Pat. Nos. 7,842,484, 8,409,640, 7,919,291, 8,470,550, 8,748,141, 8,679,793, 8,597,919, 8,702,819, 4,092,434, and 4,316,956 all of which are hereby incorporated by reference.

In the example of FIG. 1, a treatment compound (e.g. sulfur compound) is introduced into a process stream of the biorefinery operation. The treatment compound combines with the toxin to form a less toxic or non-toxic compound. Since the toxin enters the biorefinery with the grain, it is present in many of the biorefinery process streams and the treatment compound may be introduced to any of these streams to react with the toxin. For example the treatment compound may be introduced in a stream 202 that mixes with the grain 102 prior to or during milling. The treatment compound may be introduced in a stream 204 that mixes with the milled grain 106 prior to or during saccharification 108. The treatment compound may be introduced in a stream 206 that mixes with the slurry 111 prior to or during fermentation 112. The treatment compound may be introduced in a stream 208 or 210 that mixes with the beer 114 prior to or during distillation 118. The treatment compound may be introduced in a stream 212 that mixes with the whole stillage 122 prior to or during stillage separation 124. The treatment compound may be introduced in a stream 214 that mixes with the thin stillage prior to or during evaporation 130. The treatment compound may be introduced in a stream 216 or 217 that mixes with the syrup prior to or during drying 134. The treatment compound may be introduced in a stream 218 that mixes with cake prior to or during drying 134. The treatment compound may be introduced in a stream 220 that mixes with the DDGS.

While introduction of the treatment compound in any one or more of the streams 202, 204, 206, 208, 210, 212, 214, 216, 217, 218, 220 may remediate the toxin, the present inventors have found that certain factors enhance the effectiveness of the remediation. It has been found that mixing in an aqueous environment facilitates the reaction. It has likewise been found that elevated temperature facilitates the reaction. Similarly, less volume of the treatment compound solution is required if a stream is chosen in which the toxin has been concentrated. The present inventors have found that toxin levels are concentrated three to five times in DDGS in an ethanol operation. Most of the one or more toxins are concentrated via the thin stillage to syrup process stream. In addition, it may be desirable not to introduce the treatment compound into the fermentation system 112 so as not to introduce changes in the carefully controlled fermentation environment. Similarly, it may be desirable not to introduce the treatment compound into the distillation system 118 to avoid any additional material that might deposit on distillation system equipment. A portion of the thin stillage is often used as recycled water that is fed back to a prior process step, such as saccharification 108 and/or fermentation 112 as shown for example at 222, and it may be desirable to avoid recycling treatment compound to a prior process step. For these reasons, it is preferable to introduce the treatment compound into the hot, aqueous thin stillage or syrup, where most of the toxin is concentrated, after any recycled thin stillage has been drawn off for recycle water purposes but before the DDGS has been fully dried. It may also be desirable not to introduce the treatment compound into the evaporation system 130 to avoid any additional material that might deposit on evaporation equipment. It is believed that introducing the treatment compound into the syrup via stream 216 may be most advantageous. Wherever the treatment compound is introduced, the reaction may benefit from increased dwell time such as, for example, the dwell time of the syrup in the syrup storage system 133.

Figure 2:
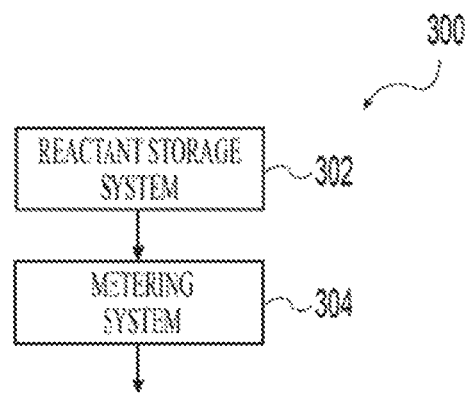
FIG. 2 is a flow diagram of a toxin remediation system.

The treatment compound may be introduced via a toxin remediation system 300 as shown in FIG. 2. In the example of FIG. 2, the toxin remediation system 300 includes a reactant storage system 302 containing an aqueous solution of the treatment compound and a metering system 304 in fluid communication with the reactant storage system 302 and the desired introduction point in the process stream. For example, the metering system 304 may connect directly to any one or more of the streams 202, 204, 206, 208, 210, 212, 214, 216, 217, 218, 220. For example, the toxin remediation system 400 of FIG. 2 may be a skid mounted self-contained unit that is inserted into an existing process stream in an existing operation to provide for toxin remediation Toxin levels may be monitored and a controller may be used to control the metering system to deliver a dose of treatment compound sufficient to reduce toxin levels to an acceptable threshold (e.g. values as reported by the US Food & Drug Administration (FDA)). Toxin levels may be monitored at any point in the biorefinery operation. For example the toxin level in incoming grain may be monitored and a dose may be calculated based on those levels. In another example, the toxin level may be monitored in the DDGS and the toxin remediation system controlled to maintain the DDGS toxin level within an acceptable range. In another example the toxin level may be monitored in a process stream upstream of the toxin remediation system and also in a process stream downstream of the toxin remediation system. Alternatively, monitoring may be omitted and a sufficient dose of treatment compound may be administered to treat maximum expected values of toxins. At times when no toxin is present the toxin remediation system can be idled to stop the flow of treatment compound to conserve treatment compound and reduce costs. For example, grain may be tested prior to entry into the biorefinery, and in crop years and regions where toxins are present above a threshold value the remediation system can be employed.

Depending on the time for reacting and the other considerations, the dosing of the treatment compound can be conducted in a batch process or a continuous process.

Figure 3:
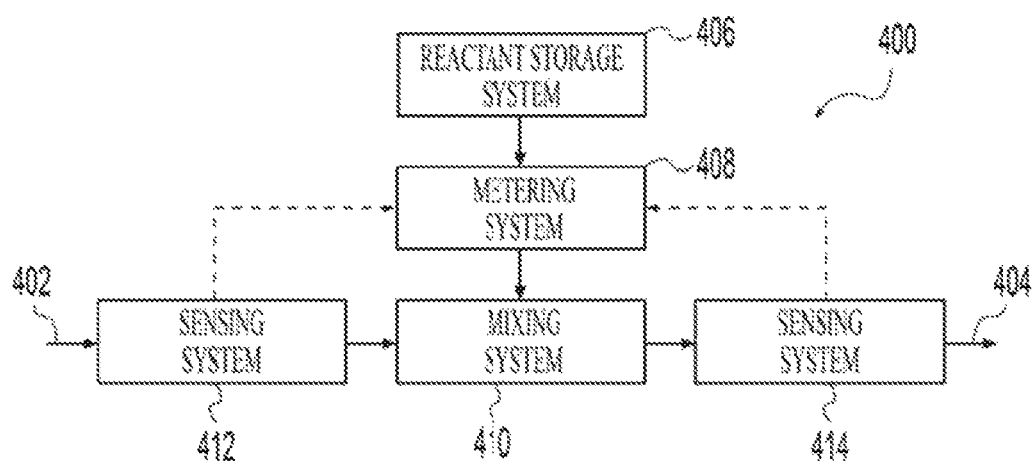
FIG. 3 is a flow diagram of a toxin remediation system connected to a process stream.
Figure 4:
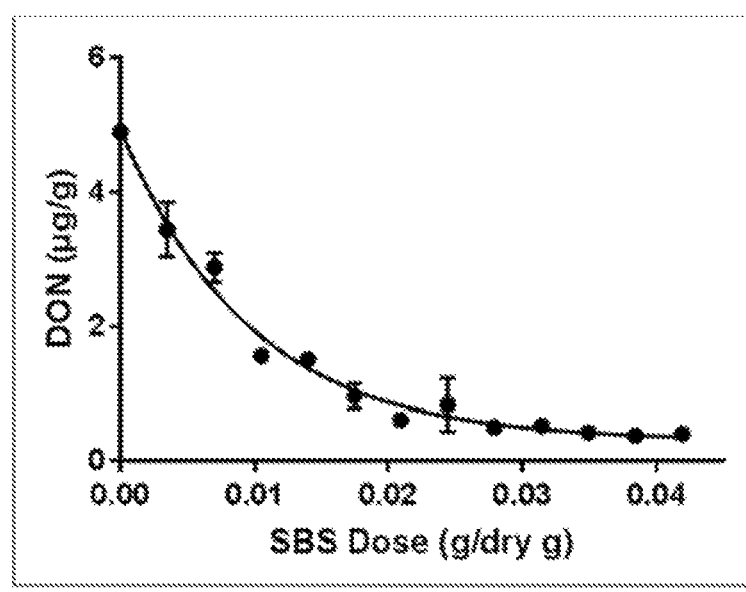
FIG. 4 is a graphical representation of sodium bisulfite dose (SBS) and deoxynivalenol (DON).
Figure 5:
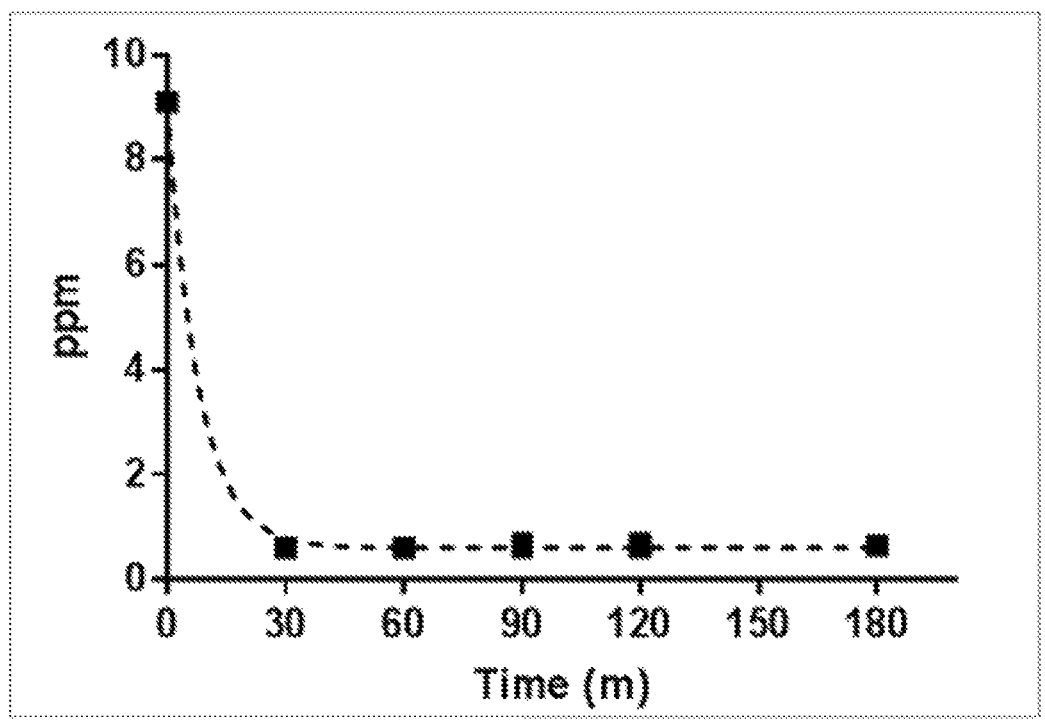
FIG. 5 is a graphical representation of reduction in DON in response to dwell time.

FIG. 3 depicts a toxin remediation system 400 configured to be connected in line with a process stream. For example, the toxin remediation system 400 of FIG. 3 may be a skid mounted self-contained unit that is inserted into an existing process stream in an existing operation to provide for toxin remediation. In the example of FIG. 3, the toxin remediation system 400 includes an inlet 402, an outlet 404, a reactant storage system 406 containing an aqueous solution of the treatment compound, a metering system 408 in fluid communication with the reactant storage system 406, and a mixing system 410 in fluid communication with the inlet 402, the metering system 410 and the outlet 404. The toxin remediation system 400 may be connected to a biorefinery operation by connecting an upstream process step to the inlet 402 and connecting the outlet 404 to a downstream process step. The toxin remediation system 400 may include one or more sensing or sampling systems 412, 414. For example the toxin level at the inlet may be monitored and communicated to the metering system 408 where it may be used to adjust the flow rate of the treatment compound. Likewise, the toxin level at the outlet may be monitored and communicated to the metering system 408 where it may be used to adjust the flow rate of the treatment compound. At times when no toxin is present the toxin remediation system can stop the flow of treatment compound to conserve treatment compound and reduce costs. The sensing or sampling systems 412, 414 are not required and it is anticipated that grain will be sampled and tested for the presence of toxins before entry into the biorefinery. Grain samples may be periodically taken and tested. Likewise, a process stream, e.g. DDGS, may be periodically tested to determine the need for and/or effectiveness of toxin remediation.

While most of the application describes the process with respect to grain, other feedstocks are also within the scope of this application. Feedstock includes seed, grains and other feedstock. For example, grains include cereal grains such as corn, wheat, barley, rice, sorghum, and rye. Further, while the production of ethanol is described, due to its particular utility as a fuel, any process that converts a feedstock into a target chemical and a nutritional co-product (e.g. animal feed) is considered within the scope of this application.

The compounds, compositions, and methods described herein can reduce or make non-toxic a variety of toxins. In embodiments, the toxin is one or more mycotoxins. Mycotoxins are toxic fungal metabolites, often found in agricultural products that are characterized by their ability to cause health problems for humans and animals. Mycotoxins include compounds such as aflatoxins, ochratoxins, patulin, fumonisins, zearalenones, and trichothecenes. They are produced for example by different *Fusarium, Aspergillus, Penicillium* and *Alternaria* species.

Examples of trichothecene mycotoxins include T-2 toxin, HT-2 toxin, isotrichodermol, diacetoxyscirpenol (DAS), 3-deacetylcalonectrin, 3, 15-dideacetylcalonectrin, scirpentriol, neosolaniol; 15-acetyldeoxynivalenol, 3-acetyldeoxynivalenol, nivalenol, 4-acetylnivalenol (fusarenone-X), 4, 15-diacetylnivalenol, 4, 7, 15-acetylnivalenol, and deoxynivalenol (DON, also known as vomitoxin), and their various acetylated derivatives. The most common trichothecene in *Fusarium* head blight is deoxynivalenol produced for example by *Fusarium graminearum* and *Fusarium culmorum*.

In embodiments, the reaction between a treatment compound and toxin results in a less toxic or non-toxic toxin. In embodiments, the treatment compound is a sulfur oxyanion. In embodiments, the treatment compound is a sulfur containing compound such as sulfate, sulfite, bisulfite, metabisulfite or combination thereof. In embodiments the treatment compound is ammonium bisulfite, potassium bisulfite, sodium bisulfite, or combination thereof.

In embodiments, the treatment compound is introduced into one or more biorefinery streams or systems by reacting the toxin and treatment compound for a dwell time of between 1 second to about 24 hours. In embodiments, the dwell time is less than 10 minutes. In embodiments, the dwell time is greater than 24 hours. In embodiments, the treatment compound is introduced into one or more biorefinery streams or systems by reacting the toxin and treatment compound for a dwell time of about 1 second to 1 minute, from about 1 minute to about 5 minutes, from about 5 minutes to 180 minutes, from about 10 minutes to 30 minutes, from about 30 minutes to 60 minutes, from about 60 minutes to 90 minutes, or from about 90 minutes to 180 minutes. In embodiments, the treatment compound is introduced into one or more biorefinery streams or systems by reacting the toxin and treatment compound for a dwell time of about 1 hour to 24 hours, from 1.5 hours to 5 hours, from 5 hours to 12 hours, or from 12 hours to 24 hours.

In embodiments, treatment compound is introduced into one or more biorefinery streams by reacting the toxin and treatment compound at a temperature from about 30° C. to 120° C., 30° C. to 60° C., 35° C. to 80° C., 45° C. to 90° C., 50° C. to 100° C., or 55° C. to 120° C. to result in a treated biorefinery process stream.

In embodiments, the treated biorefinery process streams are whole stillage, thin stillage, syrup, cake, dried distiller's grain, or combination thereof. In embodiments, the treated biorefinery process stream is syrup. In embodiments, the treated biorefinery process stream is syrup. In embodiments, the treated biorefinery process stream is dried distiller's grain with solubles (DDGS).

In embodiments, the biorefinery process stream is an aqueous stream having a solids content of less than 90%, less than 75%, less than 60%, less than 50%, less than 40%, less than 30%, less than 20%, less than 10%, less than 5% by weight. In embodiments, the biorefinery process stream has a solids content of 5-60%, 15-40%, 35-50%, 40-60% by weight.

In embodiments, the treatment compound is added to one or more biorefinery process streams from about 0.05% to about 5% weight of the biorefinery stream. In embodiments, the treatment compound includes a sulfur containing compound and the dose is limited such that the sulfur in the final product, e.g. DDGS, is no more than an acceptable threshold value. For example, the amount of sulfur in DDGS may be limited to be less than 5%; less than 3%; or even less than 1% by weight of the DDGS on a dry weight basis. In embodiments, the treatment compound dose is limited so that the sulfur in the DDGS is increased by the treatment by no more than 0.5% by weight of the DDGS on a dry weight basis.

In embodiments, the reaction is between a sulfur oxyanion and DON e.g. between a sulfite and a DON to result in a treated DON-sulfonate. In embodiments, the treatment compound is dry powdered SBS and is supplied in an amount from about 0.01 to about 0.1, e.g. from about 0.02 to about 0.05 grams SBS per dry gram syrup, or equivalent dose. In embodiments, the treatment compound is a 38% aqueous solution of SBS and is supplied in an amount from about 0.5 gallons per minute and about 2.0 gallons per minute; e.g. from about 1.0 to about 1.5 gallons per minute to a syrup stream in a commercial scale biorefinery. In embodiments, the treatment compound is a 38% aqueous solution of SBS and is supplied in an amount between 0.05% to about 5% weight of the biorefinery process stream. In embodiments, the treatment compound is a 38% aqueous solution of SBS and is supplied in an amount between 0.05% to about 5% weight of the syrup process stream.

In embodiments, the concentration of the toxin after treatment with the treatment compound is reduced by 30% or more or from about 30-99%, from 30-60%, from 45% to 75%, or from 70% to 99% of the toxin before introduction of the treatment compound.

In embodiments, the treated mycotoxin is reduced by 30% or more or from about 30-99%, from 30-50%, from 45%-75%, or from 70%-99% of the untreated, initially present toxin. In embodiments, the mycotoxin (e.g. DON) is reduced by 30% or more or from about 30-99%, from 30-50%, from 45%-75%, or from 70%-99% of the untreated, initially present toxin.

In embodiments, the mycotoxin (e.g. DON) in the treated biorefinery stream (e.g. syrup) is reduced to less than 5 ppm, less than 1 ppm, or from 5-1 ppm with a dwell time of 30 minutes. Depending on the mycotoxin and the specifications for the mycotoxin amount, the described method can also be used to reduce the mycotoxin to as low as 1 ppb.

In embodiments, the mycotoxin (e.g. DON) in the treated biorefinery process stream (e.g. syrup) reduced to less than 1 ppm at 30 minutes dwell time. It is expected that dwell times of less than 30 minutes will effectively reduce DON levels to acceptable values. For example, dwell times of less than 10 minutes, less than 5 minutes, or even less than 1 minute are expected to provide effective mycotoxin reduction. It is not necessary to reduce the DON to less than 1 ppm. For example, the FDA advises a DON limit for DDGS of 30 ppm, less than 10 ppm in total ration for ruminating beef cattle and feed lot beef cattle older than four months. The FDA advises a DON limit for DDGS of 30 ppm, less than 5 ppm in total ration for dairy cattle older than 4 months. The FDA advises a DON limit for grains and grain by-products of 5 ppm, less than 20% of diet for swine In embodiments, the DON in the treated syrup stream is reduced to less than 1 ppm at 30 minutes dwell time, less than 10 minutes, less than 5 minutes, or even less than 1 minute.

In embodiments, the DON in the treated biorefinery process stream e.g. DDGS reduced to less than 1 ppm at 30 minutes dwell time, less than 10 minutes, less than 5 minutes, or even less than 1 minute.

Remediation of toxins in biorefinery process streams according to the described process preserves the value of DDGS that would otherwise be degraded by the presence of toxins in the feedstock or grain. Such remediation may also reduce input costs to the biorefinery operation by permitting the use of grain that has been discounted due to the presence of toxins. Such remediation may also improve grain usage by facilitating the use of grain that would otherwise go to waste. The toxin remediation system described herein requires a relatively low capital investment and relatively low operating expense. The system may be monitored and metered so that it consumes treatment compound and operates equipment only when and only to the degree needed.

Additional embodiments include the following:

1. A process for remediating mycotoxin in one or more biorefinery process streams, wherein the process comprises introducing one or more treatment compounds into at least one grain biorefinery process stream to form a treated grain biorefinery process stream, wherein the at least one grain biorefinery process stream comprises a mycotoxin in a first amount, wherein the one or more treatment compounds react with the mycotoxin to form a treated mycotoxin, and wherein the treated grain biorefinery process stream comprises the mycotoxin in a second amount, wherein the second amount is less than the first amount.
2. The process of embodiment 1, wherein the treated mycotoxin is less toxic than the mycotoxin in the first amount.
3. The process as in one of embodiments 1-2, wherein the treated mycotoxin is nontoxic.
4. The process as in one of embodiments 1-3, wherein the biorefinery process stream comprises a grain-to-ethanol conversion process.
5. The process as in one of embodiments 1-4, wherein the at least one grain biorefinery process stream is produced by the steps of:
   i. milling the grain to provide a milled grain;
   ii. mixing the milled grain with water to form a slurry;
   iii. saccharifying the slurry;
   iv. fermenting the saccharified slurry with a yeast to produce a beer;
   v. separating the beer to produce an ethanol stream and a solids stream; and
   vi. drying the solids stream to produce dried distillers grain.
6. The process as in one of embodiments 1-5, wherein the at least one grain biorefinery process stream is a milled grain, a slurry, a beer, a whole stillage, a thin stillage, a syrup, a cake, a dried distiller's grain or combination thereof.
7. The process as in one of embodiments 1-6, wherein the grain is a cereal grain.

8. The process as in one of embodiments 1-7, wherein the grain is corn, wheat, rye, barley, rice or sorghum.
9. The process as in one of embodiments 1-8, wherein the mycotoxin comprises at least one aflatoxin, ochratoxin, citrinin, ergo alkaloids, patulin, or fusarium toxins.
10. The process as in one of embodiments 1-9, wherein the mycotoxin comprises at least one deoxynivalenol.
11. The process as in one of embodiments 1-10, wherein the treatment compound includes a sulfur oxyanion.
12. The process of claim 11 wherein the sulfur oxyanion is a sulfate, a sulfite, a bisulfite or a metabisulfite.
13. The process as in one of embodiments 1-12, wherein the treatment compound is an ammonium bisulfite, potassium bisulfite, sodium bisulfite, or combination thereof.
14. The process as in one of embodiments 1-13, wherein the treatment amount is between 0.05% to about 5% weight of the biorefinery process stream.
15. The process as in one of embodiments 1-14, wherein the introducing the one or more treatment compounds into the at least one grain biorefinery process stream comprises a dwell time of from 1 hour to 24 hours between the introducing and producing the dried distillers grains.
16. The process as in one of embodiments 1-15, wherein the introducing the one or more treatment compounds into the at least one biorefinery process stream is at temperatures from 30° C. to 120° C.
17. The process as in one of embodiments 1-16, wherein the one or more biorefinery process stream comprises 5 to 60% solids by weight.
18. The process as in one of embodiments 1-17, wherein the mycotoxin in the second amount is reduced by 30% or more as compared to the mycotoxin in the first amount.
19. The process as in one of embodiments 1-18, wherein the treated grain biorefinery process stream is a whole stillage, thin stillage, syrup or combination thereof.
20. The process as in one of embodiments 1-19, wherein the treated grain biorefinery process stream has a concentration of mycotoxin of less than 5 ppm.
21. The process as in one of embodiments 1-20, wherein the treated mycotoxin comprises a deoxynivalenol sulfonate.
22. A composition produced by the process as in one of embodiments 1-21.
23. A system for remediating toxins comprising:
   a reactant storage system comprising one or more treatment compounds; and
   a metering system in fluid communication with the reactant storage system, wherein the system is adapted to be coupled to one or more grain biorefinery process streams to add a controlled amount of the one or more treatment compounds into the one or more grain biorefinery process streams, to produce a treated grain biorefinery process stream, wherein the at least one grain biorefinery process stream comprises a mycotoxin in a first amount, wherein the one or more treatment compounds reacts with the mycotoxin to form a treated mycotoxin, and wherein the treated grain biorefinery process stream comprises the mycotoxin in a second amount, wherein the second amount is less than the first amount.
24. The system of claim 23 further comprising a mixing system in fluid communication with an inlet and an outlet of one or more grain biorefinery process streams and the metering system.
25. The system as in one of embodiments 23-24 further connected to one or more of:
   a milling system, wherein the milling system mills a feedstock to provide a milled material;
   a saccharification system for converting the slurry into sugar, wherein the saccharification system is in fluid communication with the milling system;
   a fermentation system comprising yeast and in fluid communication with the saccharification system, the fermentation system converts the sugar into a beer;
   a distillation system in fluid communication with the fermentation system,
wherein the distillation system can distill the beer to form a distillate comprising the alcohol and a solids stream; and
   a separation system in fluid communication with the solid stream to produce dried distillers grain.

EXAMPLE 1

Experiments were performed that demonstrated that sodium bisulfite (SBS) was effective at reducing the measurable quantity of deoxynivalenol (DON) in syrup by the NEOGEN™ VERATOX™ for DON 2/3 kit. Initial testing resulted in reductions in DON. Treating syrup with SBS at process temperatures for extended time periods resulted in a DON reduction of greater than 85% in the syrup stream. Encouraged by these initial test results, further testing was performed utilizing a design of experiments to determine an equation modeling the effect of time, temperature, and SBS in the treatment of syrup. Syrup from a corn ethanol biorefinery was obtained and processed in the laboratory. All thermal treatments were performed utilizing a Parr 4560 reactor and a combined total of 70 g of syrup and SBS per reaction. Reaction conditions were from 85° C. to 115° C.; for 2 to 6 hours; and 0 to 0.05 g sodium bisulfite per dry gram syrup. The results from this study indicated a correlation between the SBS loading and the reduction in syrup DON. The model predicts a greater than 85% reduction in syrup DON is likely if treatment in a commercial process syrup tank is utilized. It was calculated that at a plant that is currently producing DDGS with 14.5 ppm DON with a 95% reduction in syrup DON would produce DDGS with 4.6 ppm DON.

EXAMPLE 2

Syrup from a corn ethanol biorefinery was obtained and processed in the laboratory. Treatment was performed utilizing a Parr 4560 reactor and a combined total of 70 g of syrup and SBS per reaction. The reaction condition was carried out at 50° C. for 120 minutes and varying amounts of sodium bisulfite per dry gram syrup. The DON was measured by NEOGEN™ VERATOX™ for DON 2/3 kit.

FIG. 4 showed that as the SBS dose increased, the DON was reduced in the treated syrup.

EXAMPLE 3

Syrup from a corn ethanol biorefinery was obtained and processed in the laboratory. Treatment was performed utilizing a Parr 4560 reactor and a combined total of 70 g of syrup and SBS per reaction. The reaction condition was carried out at 85° C. for 30 minutes to 180 minutes using 0.048 grams sodium bisulfite per dry gram syrup. The DON was measured by NEOGEN™ VERATOX™ for DON 2/3 kit.

FIG. 5 showed that the DON in the treated syrup reduced to less than 1 ppm at 30 minutes dwell time.

EXAMPLE 4

Syrup from a corn ethanol biorefinery was obtained and processed in the laboratory using a Parr 4560 reactor and combined with either 0.048 grams of SBS or ammonium bisulfite per dry gram of syrup. Ammonium bisulfite was a 65% aqueous solution of 95% ammonium bisulfite and 5% potassium bisulfite. The doses of the two reagents used were molar equivalent bisulfite doses. The reaction condition was carried out at 85° C. for 30, 60 and 90 minutes.

Figure 6:
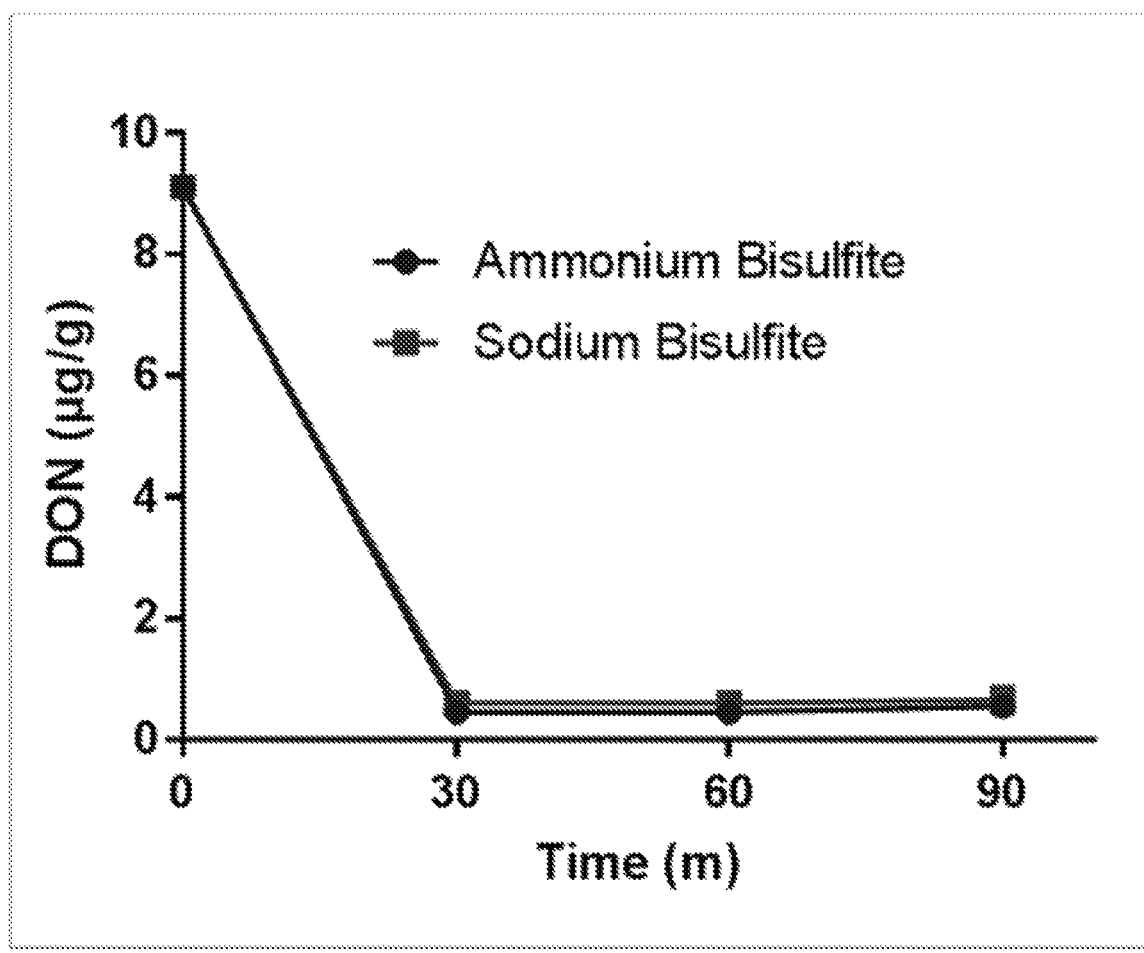
FIG. 6 is a graphical representation of DON amount in syrup for two different bisulfites.

FIG. 6 showed reduction of DON in syrup with ammonium bisulfite was similar to sodium bisulfite.

EXAMPLE 5

Figure 7:
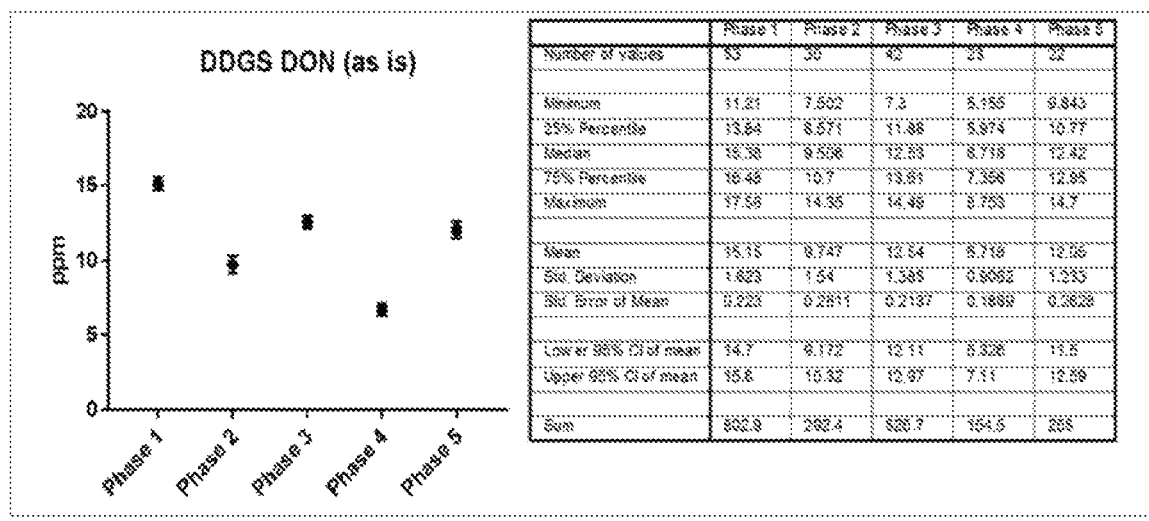
FIG. 7 is a graphical representation of DON present in DDGS in a grain-to-ethanol conversion process.

A test of SBS treatment in a grain-to-ethanol conversion process was performed in phases in which treatment was not conducted, and phases in which treatment was conducted. The data is shown in FIG. 7. Syrup was fed through a feed line into a syrup tank. The syrup was fed from the syrup tank to the dryers where it combined with wet cake and was dried to produce DDGS. In Phase 1, no treatment was conducted and samples of dried DDGS were collected and analyzed to measure the ppm of DON present. In Phase 2, 1.5 gallons per minute of a 38% aqueous solution of SBS was supplied continuously into the feed line of the syrup tank and samples of dried DDGS were collected and analyzed to measure the ppm of DON present. In Phase 3, the flow of SBS was stopped and again untreated samples of dried DDGS were collected and analyzed to measure the ppm of DON present. In Phase 4, 1 gallon per minute of a 38% aqueous solution of SBS was supplied continuously into the feed line of the syrup tank and samples of dried DDGS were collected and analyzed to measure the ppm of DON present. FIG. 7 showed that the amount of DON in the DDGS was reduced by approximately 40% to 50% when the SBS treatment system was in operation.

EXAMPLE 6

A treated mycotoxin in which the DON levels in DON-contaminated DDGS were reduced by the method described in Example 5 (1.5 gallons per minute of a 38% aqueous solution of SBS was supplied continuously into the feed line of the syrup tank) and samples of dried DDGS were collected, analyzed and tested for its effect on pig growth.

A total of 247 growing pigs (55.3±4.6 lb.) were housed at a wean-to-finish facility, randomly allotted to 18 pens (13-14 pigs/pen) containing one 3-hole feeder 2 free-access nipple drinkers, and assigned to one of 3 experimental diets: control, DONDDGS, and treated-DDGS. All experimental diets were corn/soybean meal based containing 30% DDGS (low DON, DON contaminated, and treated DON DDGS, respectively; Table 1).

TABLE 1

Levels of DON in the corn, DDGS sources and mixed diets on d0 and 21[1].

| Item | DON, ppm |
| --- | --- |
| Corn | 0.1 |
| Clean DDGS (Control) | 1.0 |
| Treated DDGS (trtDDGS) | 7.3 |
| Untreated DDGS (DONDDGS) | 11.6 |

TABLE 1-continued

Levels of DON in the corn, DDGS sources and mixed diets on d0 and 21[1].

| Item | DON, ppm |
| --- | --- |
| d0 mixed diets | |
| Control | 0.1 |
| trtDDGS | 1.9 |
| DONDGGS | 3.0 |
| d21 mixed diets | |
| Control | 0.2 |
| trtDDGS | 2.6 |
| DONDDGS | 3.0 |

[1]The DON value for corn is the mean of 3 corn samples (1 sample from each of the experimental diets). Diet samples were taken at mixing (d0) and from each feeder at the completion of the trial (d21).

All diets met or exceeded nutrient requirements for growing pigs based on NRC (2012) and provided ad libitum. Experimental diets were fed for 21 days. Samples of the DDGS and corn used in the diets were analyzed for DON. Samples of the mixed diets were collected at day 0 and 21 and analyzed for proximate analysis and DON.

Pigs were weighed individually on day 0, 3, 7, 10, 14, and 21. Feed disappearance was determined simultaneously with pig weight.

Statistical Analysis

Performance data were analyzed using the PROC MIXED procedure of SAS (Version 9.4; SAS Inst. Inc., Cary, N.C.) as a repeated measures model with pen as the random variable, weigh period as the repeated variable, and dietary treatment was the fixed effect. Weekly performance responses were analyzed as a completely random design where differences between treatment means were tested using Tukey's adjusted means test when a significant main effect was observed. Results were considered significant at $P<0.05$ and tendency at $0.05 \geq P \leq 0.10$.

Evidence of vomiting was observed within 4 hours of the experimental diets being available and was observed only in the DONDDGS pens. Vomiting was not observed beyond the first 24 hours of starting the trial. Otherwise, pig health was good with only 1 pig removed prior to the last day due to poor growth after repeated veterinary treatment.

Diet Mycotoxin Content

Negligible DON content was measured in the ground corn used for the experimental diets. The level of DON in the 'clean' DDGS resulted in a DON level below the FDA recommended level (no greater than 1 ppm) in the control diet. The sodium bisulfite treatment appeared to be effective at reducing the DON content in DON-DDGS by 37%, resulting in diet DON content of 1.9 ppm. The level of DON appeared stable in the control and DONDDGS diets with some increase in DONDDGS levels in the trtDDGS diet by the end of the 21 days.

Pig Performance

There was no main effect of diet on daily gain but a tendency ($P=0.084$) for an interaction between weigh period and diet where daily gain was not different between each weight period and lower ($P \leq 0.05$) in the first 3 days in pigs fed DONDDGS and trtDDGS compared to other weigh periods. Daily feed intake increased over time ($P<0.0001$) and there was a tendency ($P=0.071$) for DONDDGS-fed pigs to have lower ($P=0.029$) overall intake compared to trtDDGS-fed. Overall intake was not different between trtDDGS- and Control-fed pigs.

The invention claimed is:

1. A process for remediating mycotoxin in one or more biorefinery process streams, wherein the process comprises:
introducing one or more treatment compounds into at least one biorefinery process stream to form a treated biorefinery process stream, wherein the at least one biorefinery process stream is chosen from thin stillage, syrup and combinations thereof, wherein the one or more treatment compounds comprises one or more sulfur-containing compounds, wherein the at least one biorefinery process stream comprises one or more mycotoxins, wherein the one or more treatment compounds react with the one or more mycotoxins in the at least one biorefinery process stream to form the treated biorefinery process stream, and wherein the treated biorefinery process stream is less toxic than the at least one biorefinery process stream.

2. The process of claim 1, wherein the at least one biorefinery process stream is produced in a grain-to-ethanol conversion process that also includes the steps of:
i. milling grain to provide a milled grain;
ii. mixing the milled grain with water to form a slurry;
iii. saccharifying the slurry;
iv. fermenting the saccharified slurry with a yeast to produce a beer;
v. separating the beer to produce an ethanol stream and whole stillage; and
vi. separating the whole stillage into thin stillage and wet cake; and
vii. concentrating thin stillage into syrup.

3. The process of claim 2, wherein the one or more treatment compounds react with the one or more mycotoxins in the at least one biorefinery process stream for a dwell time from 1 hour to 24 hours.

4. The process of claim 1, wherein the at least one biorefinery process stream is a syrup stream.

5. The process of claim 1, wherein the one or more mycotoxins comprises at least one of zearalenone, deoxynivalenol, and fumonisin.

6. The process of claim 1, wherein the treatment compound is chosen from a sulfate, a sulfite, a bisulfite, a metabisulfite and combinations thereof.

7. The process of claim 1, wherein the treatment compound is chosen from ammonium bisulfite, potassium bisulfite, sodium bisulfite and combinations thereof.

8. The process of claim 1, wherein the treatment compound amount is between 0.05% to about 5% weight of the at least one biorefinery process stream.

9. The process of claim 1, wherein the introducing the one or more treatment compounds into the at least one biorefinery process stream occurs while the at least one biorefinery process stream is at temperatures from 30° C. to 120° C.

10. The process of claim 1, wherein the at least one or more biorefinery process stream comprises 5 to 60% solids by weight.

11. The process of claim 1, wherein the one or more mycotoxins comprises deoxynivalenol.

12. The process of claim 11, wherein the one or more treatment compounds react with the deoxynivalenol in the at least one biorefinery process stream to form deoxynivalenol sulfonate wherein the deoxynivalenol the treated biorefinery process stream is reduced by 30% or more as compared to the deoxynivalenol in the at least one biorefinery process stream.

13. The process of claim 1, wherein the one or more mycotoxins in the treated biorefinery process stream is less than 5 ppm.

14. The process of claim 1, wherein the one or more treatment compounds is introduced into the at least one biorefinery process stream in a tank.

15. The process of claim 1, wherein the treated biorefinery process stream is combined with wet cake.

16. The process of claim 15, wherein the treated biorefinery process stream combined with wet cake is dried to form dried distillers grain with solubles (DDGS).

17. The process of claim 1, wherein the introducing the one or more treatment compounds into the at least one biorefinery process stream occurs while the at least one biorefinery process stream is at temperatures from 55° C. to 120° C.

18. The process of claim 1, wherein the one or more treatment compounds are introduced into the thin stillage stream, wherein a portion of the thin stillage stream is recycled to fermentation, saccharification or both before introducing one or more treatment compounds into the thin stillage stream.

* * * * *